(12) United States Patent
Matsuoka et al.

(10) Patent No.: US 8,188,333 B2
(45) Date of Patent: May 29, 2012

(54) PLASTIC SHEET LOOKING LIKE CLOTH AND SURFACE MATERIAL OF ABSORBING GOODS UTILIZING THE SHEET, AND MANUFACTURING METHOD THEREOF

(75) Inventors: Masaki Matsuoka, Shizuoka (JP); Masaya Fujita, Shizuoka (JP)

(73) Assignee: Daio Paper Corporation, Ehime (JP)

( * ) Notice: Subject to any disclaimer, the term of this patent is extended or adjusted under 35 U.S.C. 154(b) by 1323 days.

(21) Appl. No.: 10/130,400

(22) PCT Filed: Sep. 13, 2001

(86) PCT No.: PCT/JP01/07941
§ 371 (c)(1),
(2), (4) Date: May 14, 2002

(87) PCT Pub. No.: WO02/22344
PCT Pub. Date: Mar. 21, 2002

(65) Prior Publication Data
US 2003/0004481 A1    Jan. 2, 2003

(30) Foreign Application Priority Data

Sep. 14, 2000 (JP) .................................. 2000-279034
Dec. 11, 2000 (JP) .................................. 2000-375607

(51) Int. Cl.
*A61F 13/15* (2006.01)
*B29C 65/00* (2006.01)
*B29C 55/00* (2006.01)
*B29C 33/58* (2006.01)
*B29C 59/02* (2006.01)

(52) U.S. Cl. ......... 604/370; 604/378; 604/380; 604/383; 604/365; 604/366; 156/495; 156/229; 156/252; 264/292; 264/316; 264/320

(58) Field of Classification Search ................. 604/378, 604/370, 380, 383, 365, 366; 156/495, 229, 156/252; 264/292, 316, 320
See application file for complete search history.

(56) References Cited

U.S. PATENT DOCUMENTS

| 3,047,444 | A | * | 7/1962 | Harwood | 428/153 |
| 4,100,324 | A | * | 7/1978 | Anderson et al. | 442/344 |
| 4,588,630 | A |   | 5/1986 | Shimalla | 428/131 |
| 4,692,368 | A | * | 9/1987 | Taylor et al. | 428/137 |
| D375,844  | S | * | 11/1996 | Edwards et al. | D5/47 |
| 5,964,742 | A | * | 10/1999 | McCormack et al. | 604/380 |

(Continued)

FOREIGN PATENT DOCUMENTS

EP    313766 A2    5/1989

(Continued)

OTHER PUBLICATIONS

Abstract of JP 2000-100585, published 1998, Patent Abstracts of Japan, 1 page.

(Continued)

*Primary Examiner* — Jacqueline F. Stephens
(74) *Attorney, Agent, or Firm* — Sughrue Mion, PLLC

(57) ABSTRACT

A plastic sheet having cloth-like appearance and thermoplasticity and provided with melt patterns in the sheet face, the melt patterns formed in a predetermined arrangement under an elongating condition of the plastic sheet so as to form convex-concave wrinkles in regions between neighboring melt patterns in the plastic sheet under an un-elongating condition.

10 Claims, 14 Drawing Sheets

U.S. PATENT DOCUMENTS 6,632,504 B1 * 10/2003 Gillespie et al. ............ 428/131

FOREIGN PATENT DOCUMENTS

| JP | 4-152945 | 5/1992 |
| --- | --- | --- |
| JP | 5-300922 | 11/1993 |
| JP | 6-166111 | 6/1994 |
| JP | 11-89879 | 4/1999 |
| JP | 11-291376 | 10/1999 |
| JP | 2000-100585 | 4/2000 |
| JP | P2001-146674 A | 5/2001 |
| WO | WO 94/20054 | 9/1994 |
| WO | 99/62449 | 12/1999 |

OTHER PUBLICATIONS

English Translation of JP 2859725, 11 pages.

* cited by examiner

PLASTIC SHEET LOOKING LIKE CLOTH AND SURFACE MATERIAL OF ABSORBING GOODS UTILIZING THE SHEET, AND MANUFACTURING METHOD THEREOF

TECHNICAL FIELD

The present invention relates to a plastic sheet having the appearance and the touch just like a cloth by artificially wrinkling the sheet surface as to have convex-concave surface, a surface material of an absorptive product using the plastic sheet and a manufacturing method of the plastic sheet.

BACKGROUND ART

Conventionally, as a surface material of an absorptive product, provided on the market are those which are provided with proper melt patterns (embossed patterns) depending on a variety of the purpose such as the purposes of suppressing the wet feeling by decreasing the surface area contacting the skin or giving the quality feeling and at the same time improving the sensuous touch or the like. As such a kind of material, examples are those disclosed in Japanese Patent Application Laid-open No. 10-272152 A, Japanese Patent No. 2859725 C1 and the like.

The surface material disclosed in the former Japanese Patent Application Laid-open No. 10-272152 A is composed of a thermally fusible hydrophobic upper layer sheet having a large number of liquid-leading opening parts and a thermally fusible hydrophilic under layer sheet disposed in the inner face of the upper layer sheet and the upper layer and the under layer sheets are thermally bonded to each other by a large number of emboss patterned dents or holes with specified shapes and the surface material disclosed in the latter Japanese Patent No. 2859725 C1 is provided with a plurality of hollow projected stripes extended in the longitudinal direction at proper distance from one another in the width direction and a plurality of opening holes for liquid permeation formed in each space between the foregoing neighboring hollow projected stripes.

However, although the surface material produced by melting in spots of a large number of dotted embossed holes and thermally bonding an upper layer sheet and the under layer sheet just like the surface material disclosed in the foregoing Japanese Patent Application Laid-open No. 10-272152 A is provided with dotted patterns with the dispersed dents and holes, the problem is not solved that the surface material is insufficient in solid impression and gives the cool appearance and touch which smooth plastic face gives as an impression.

On the other hand, in the case of the surface material disclosed in the foregoing Japanese Patent 2859725 C1, since it has clear hollow projected stripes in the surface layer, the surface material is cubic and does not have a cool impression of cool as the entire impression. However, there are the following problems: the foregoing hollow projected stripes are easy to be crushed by being pressurized from the body side and the crushed hollow projected stripes clog the opening holes for liquid permeation or the hollow projected stripes are easy to be loosened and extremely inferior in shape stability.

Therefore, a first object of the present invention is to provide a plastic sheet provided with a cloth-like appearance and touch although a plastic sheet forming convex-concave (unevenness) wrinkles on the sheet surface.

Further, a second object of the present invention is to provide a surface material of an absorptive product with heightened wrinkle shape stability while giving the soft, gentle and warm impression and touch by utilizing the advantage of the plastic sheet surface material, that is, "dry touch after liquid permeation" and also to provide an absorptive product using the surface material.

A third object of the present invention is to provide a plastic sheet and a surface material having such cloth-like appearance for an absorptive product and further to provide a method for manufacturing an absorptive product using the surface material.

DISCLOSURE OF THE INVENTION

A plastic sheet having the cloth-like appearance according to the first invention to solve the foregoing first object is a plastic sheet having thermoplasticity and provided with melt patterns in the sheet face, in which the melt patterns are formed in predetermined arrangement under the elongating condition of the plastic sheet so as to form the convex-concave wrinkles in regions between neighboring melt patterns in the plastic sheet under the un-elongating condition.

A plastic sheet having the cloth-like appearance according to the second invention to solve the foregoing first object is a plastic sheet having thermoplasticity and provided with melt patterns in the sheet face in which the melt patterns are formed under the elongating condition of the plastic sheet so as to make virtual lines (7) bonding the regions-where no melt pattern is formed in approximately the elongation direction be linearly discontinuous and zigzag or diamond patterns and so as to form the convex-concave wrinkles corresponding to the melt patterns in the plastic sheet under the un-elongating condition.

A plastic sheet having the cloth-like appearance according to the third invention to solve the foregoing first object is a plastic sheet having thermoplasticity and provided with melt patterns in the sheet face in which the melt patterns are formed under the elongating condition of the plastic sheet and composed of at least two types of melt pattern groups; a group of holding patterns for holding the elongation state and having the longitudinal size practically in the elongation direction and a group of disconnection patterns having the longitudinal size in the direction practically perpendicular to the elongation direction and shutting diffusion of the strains owing to the holding patterns in the elongation direction, so as to make virtual lines (7) bonding the regions where no melt pattern is formed in approximately the elongation direction be linearly discontinuous and zigzag or diamond patterns and so as to form the convex-concave wrinkles corresponding to the melt patterns in the plastic sheet under the un-elongating condition.

A plastic sheet having the cloth-like appearance according to the fourth invention to solve the foregoing first object is a plastic sheet having thermoplasticity and provided with melt patterns in the sheet face in which the melt patterns are formed under the elongating condition of the plastic sheet by reciprocally repeating rows of holding patterns (1) formed like columns at predetermined intervals in the direction perpendicular to the elongation direction and practically having the longitudinal size in the elongation direction to hold the elongation state and rows of disconnecting patterns (2) formed like columns positioned between respectively neighboring patterns of the rows of the holding patterns at predetermined intervals in the direction perpendicular to the elongation direction and practically having the longitudinal size in the direction perpendicular to the elongation direction to shut the diffusion of the strains owing to the holding patterns (1) in the elongation direction so as to form the convex-concave wrinkles corresponding to the melt patterns in the plastic sheet under the un-elongating condition.

In this case, the longitudinal size of the holding patterns (1) in the elongation direction is preferably in a range of 1.5 mm to 7 mm.

Further, a plastic sheet having the cloth-like appearance according to the fifth invention to solve the foregoing first object is a plastic sheet having thermoplasticity and provided with melt patterns in the sheet face in which the melt patterns are formed under the elongating condition of the plastic sheet by repeating rows of melt patterns each composed of holding patterns (3) formed at predetermined intervals in the direction perpendicular to the elongation direction and practically having the longitudinal size in the elongation direction to hold the elongation state and disconnecting patterns (4) practically having the longitudinal size in the direction perpendicular to the elongation direction to shut the diffusion of the strains owing to the holding patterns (3) in the elongation direction in a manner of forming the zigzagged pattern state in the elongation direction, so as to form the convex-concave wrinkles corresponding to the melt pattern arrangements in the plastic sheet face under the un-elongating condition.

A plastic sheet having the cloth-like appearance according to the sixth invention to solve the foregoing first object is a plastic sheet having thermoplasticity and provided with melt patterns in the sheet face in which the melt patterns are formed under the elongating condition of the plastic sheet by reciprocally repeating rows of first melt patterns (5) formed like columns at predetermined intervals in the direction perpendicular to the elongation direction and practically having the longitudinal size in the direction slanting to the elongation direction and rows of second melt patterns (6) formed like columns positioned between respectively neighboring patterns of the rows of the first patterns at predetermined intervals in the direction perpendicular to the elongation direction and practically having the longitudinal size in the direction crossing the elongation direction and the slanting direction of the first melt patterns (5) so as to form the convex-concave wrinkles corresponding to the melt patterns in the plastic sheet under the un-elongating condition.

A plastic sheet having the cloth-like appearance according to the seventh invention to solve the foregoing first object is a plastic sheet having thermoplasticity and provided with melt patterns in the sheet face, in which the melt patterns are formed in non-lattice-like arrangement of predetermined shape or designed patterns (8) under the elongating condition of the plastic sheet so as to form the convex-concave wrinkles corresponding to the melt pattern arrangement in the plastic sheet under the un-elongating condition.

In order to provide the liquid permeability to the above described plastic sheets having the cloth-like appearance according to the present invention, a large number of opening holes (18) are formed in the sheet face.

The plastic sheets having such characteristics provide comfortable the skin touch and warm cloth-like appearance, which a product using a conventional plastic sheet never has, in an absorptive product comprising a liquid permeable surface material, a liquid impermeable rear face material, and an absorptive body inserted between them by being utilized as at least one of the surface material, the rear face material and an absorption body.

Next, a surface material of an absorptive product according to the first invention to solve the second object is a thermoplastic plastic sheet surface material to be disposed in the use face side with which the skin of a user contacts in the absorptive product and is characterized by having a large number of liquid permeable opening holes (18) and inter-opening regions disposed between respectively neighboring opening holes and being provided with melt patterns formed in the area covering the opening holes and the inter-opening regions under the elongating condition so as to form wrinkles in inter-opening regions under the un-elongating condition owing to the melt patterns.

Further, a surface material of an absorptive product according to the second invention to solve the second object is a thermoplastic plastic sheet surface material to be disposed in the use face side with which the skin of a user contacts in the absorptive product and is characterized by having a large number of liquid permeable opening holes (18) and inter-opening regions disposed between respectively neighboring opening holes and characterized in that in at least some parts of the surface material, melt pattern columns each including the liquid permeable opening holes and inter-opening regions and having clear difference among pattern forms are reciprocally repeated along a predetermined direction of the surface material under the elongating condition so as to form the convex-concave wrinkles corresponding to the arrangement of the melt patterns.

Incidentally, the term, including, means that the melt patterns are formed without discriminating the opening regions and the inter-opening regions to be formed in the surface material. The melt patterns and the wrinkles corresponding to the arrangement of the melt patterns are preferably formed at least in the center part of the absorptive product in the longitudinal direction equivalent to the body fluid discharge part in terms of decreasing the wet feeling after liquid permeation.

However, at the same time, in order to have the cloth-like appearance, it is further preferable to form them not partially but in entire face of the surface material.

As described above, since the foregoing plastic sheet and surface material of an absorptive product are provided with the convex-concave wrinkles corresponding to the melt pattern arrangements, the cloth-like appearance and touch can be obtained and since the hills and valleys of the wrinkles correspond to the melt pattern arrangements, the wrinkles are hard to be loosened and thus have high shape stability. At the same time, the light refection directions are irregularly changed, so that the luster and cool flat impression, which a resin sheet material characteristically gives, is suppressed, and the appearance and the touch are made similar to the cloth-like appearance and the cloth-like touch. Especially, owing compounded effects of the pale shadows due to the relatively small projected parts and recessed parts caused by the foregoing melt patterns and the relatively dark shadows owing to the wrinkles observed in the surface material when being seen from the diagonal direction, the plastic sheet and the surface material of an absorptive product show gentle cloth-like appearance and seem unlike a synthetic resin sheet.

The light reflectance in the skin-contacting face side of the foregoing plastic sheet and the surface material is preferably 5% or lower to have cloth-like appearance. Further, the apparent thickness of the surface material containing the hill parts and the valley parts of the wrinkles and the intervals between reciprocally neighboring hills or valleys of the wrinkles are preferably respectively 5 mm or thinner and 10 mm or narrower.

Further, the absorptive product according to the present invention to solve the foregoing second object is characterized by comprising the foregoing liquid-permeable surface material, a liquid-impermeable rear face sheet and an absorptive body inserted between them.

A manufacturing method of the plastic sheet having the cloth-like appearance according to the present invention to solve the foregoing third object is characterized by forming melt patterns by a melt pattern-forming roll (105) heated to a softening point of the plastic sheet having thermoplasticity while keeping the plastic sheet elongated by 5 to 40% in a manner that virtual lines bonding the regions where no melt pattern is formed in approximately the elongation direction are made to be linearly discontinuous and zigzag or diamond patterns.

A manufacturing method of the surface material of the absorptive product according to the present invention to solve the foregoing third object is characterized by forming a large number of holes in a plastic sheet having thermoplasticity by a hole-forming roll (104) in which a large number of holes are arranged and after that, forming melt patterns by a melt pattern-forming roll (105) heated to a softening point of the plastic sheet while keeping the plastic sheet elongated by 5 to 40% in a manner that virtual lines bonding the regions where no melt pattern is formed in approximately the elongation direction are made to be linearly discontinuous and zigzag or diamond patterns.

As described above, according to the present invention, forming convex-concave wrinkles on the surface makes it possible to obtain a plastic sheet provided with the appearance and the touch just like a cloth though a plastic sheet.

As a result, while keeping the advantage of a plastic sheet surface material, that is, "the dry touch property after permeation of the body fluid", as it is, it is made possible to obtain the soft, gentle and warm appearance and touch and also increase the shape stability of the wrinkles.

A manufacturing method of an absorptive product according to the present invention to solve the foregoing third object is characterized by comprising a step of producing a surface material of the absorptive product by forming a large number of holes in a plastic sheet having thermoplasticity by a hole-forming roll (104) in which a large number of holes are arranged and after that, forming melt patterns by a melt pattern-forming roll (105) heated to a softening point of the plastic sheet while keeping the plastic sheet elongated by 5 to 40% in a manner that virtual lines bonding the regions where no melt pattern is formed in approximately the elongation direction are made to be linearly discontinuous and zigzag or diamond patterns, and after that turning the elongation state back to non-elongation state; a step of sending a rear face sheet (11) out of a rear face sheet supply drum (103); and a step of sending an absorptive unit (13) between the foregoing surface material and the rear face sheet and integrally laminating them.

BEST MODE FOR CARRYING OUT THE INVENTION

Hereinafter, the best modes to achieve the invention will be described in details with the reference of the drawings.
<A plastic Sheet Having Cloth-like Appearance>

A plastic sheet according to the present invention is provided with convex-concave (unevenness) wrinkles in the surface so as to have the appearance and the touch just like a cloth though a plastic sheet.

For the plastic sheet, usable as a material is a synthetic resin sheet showing thermoplasticity. As such a synthetic resin sheet, preferable to be used are olefin type resin such as polyethylene, polypropylene and the like and also usable are polyamide type resin such as nylon, and ethylene-vinyl copolymer (EVA). The plastic sheet is especially used for a part to be brought into contact with the skin and preferable to be used for a surface material to be brought into contact with the skin and the surface material is further preferable to be used for an absorptive product.

The foregoing convex-concave wrinkles can be exemplified, as wrinkles formed irregularly in the plastic sheet face just like wavy ridges. Generally, the convex-concave wrinkles can be formed by forming melt patterns under the elongating condition of a plastic sheet so as to make virtual lines bonding the regions where no melt pattern is formed in approximately the elongation direction be linearly discontinuous but continuous in zigzag or diamond patterns and so as to generate undulation owing to strains and form convex-concave wrinkles corresponding to the melt patterns.

Hereinafter, the formation modes of the foregoing respective convex-concave wrinkles will be practically and separately described in details.
[The First Formation Mode]

Figure 1A:
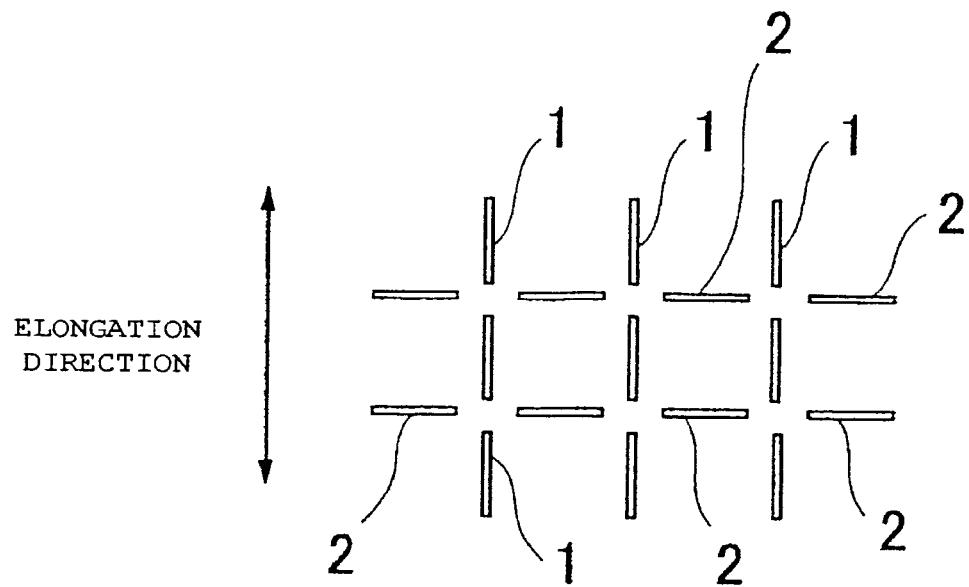
FIGS. 1A and 1B are plan views showing the first embodiment of melt patterns.
Figure 1B:
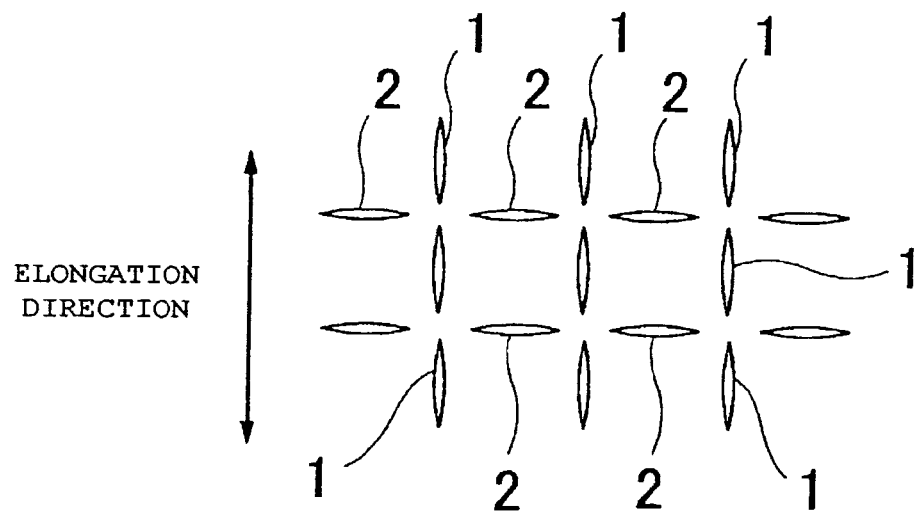

Regarding the convex-concave wrinkles according to the first formation mode, as shown in FIG. 1A and FIG. 1B, the melt patterns compose melt pattern arrangements formed by reciprocally repeating in the elongation direction rows of holding patterns 1 formed like columns at predetermined intervals in the direction perpendicular to the elongation direction and having the longitudinal size practically in the elongation direction and rows of disconnecting patterns 2 at predetermined intervals from one another in the direction perpendicular to the elongation direction and formed like columns between neighboring rows of the foregoing holding patterns 1 and having the longitudinal size practically in the direction perpendicular to the elongation direction.

Regarding the melt patterns representatively shown in FIG. 1A, based on FIG. 2, the formation principle of the convex-concave wrinkles will be described as follows: if the melt patterns composed of the foregoing holding patterns 1 and disconnecting patterns 2 are formed while keeping a plastic sheet elongated, the sections where the foregoing holding patterns 1 are formed are fixed as being elongated as they are and keep the elongated state even after the tension is released, whereas the regions sandwiched between neighboring holding patterns 1 and having no melt pattern formed tend to restore the original state. The strains generated at that time tend to diffuse in the peripheral parts but cannot be diffused in the side (in the direction perpendicular to the elongation direction) owing to the holding patterns 1 positioned in both sides and since the foregoing disconnecting patterns 2 to disconnect the release of the strains are disposed in the up and down direction (in the elongation direction), the diffusion direction of the strains goes through between the holding patterns 1 and the disconnecting patterns 2, in other words, the diffusion direction goes in the diagonal direction to diffuse the strains and at the same time many of strains remain internally as residual strains, so that, as shown in FIG. 3, irregularly undulated projected parts and recessed parts are formed to form wrinkles.

Figure 2:
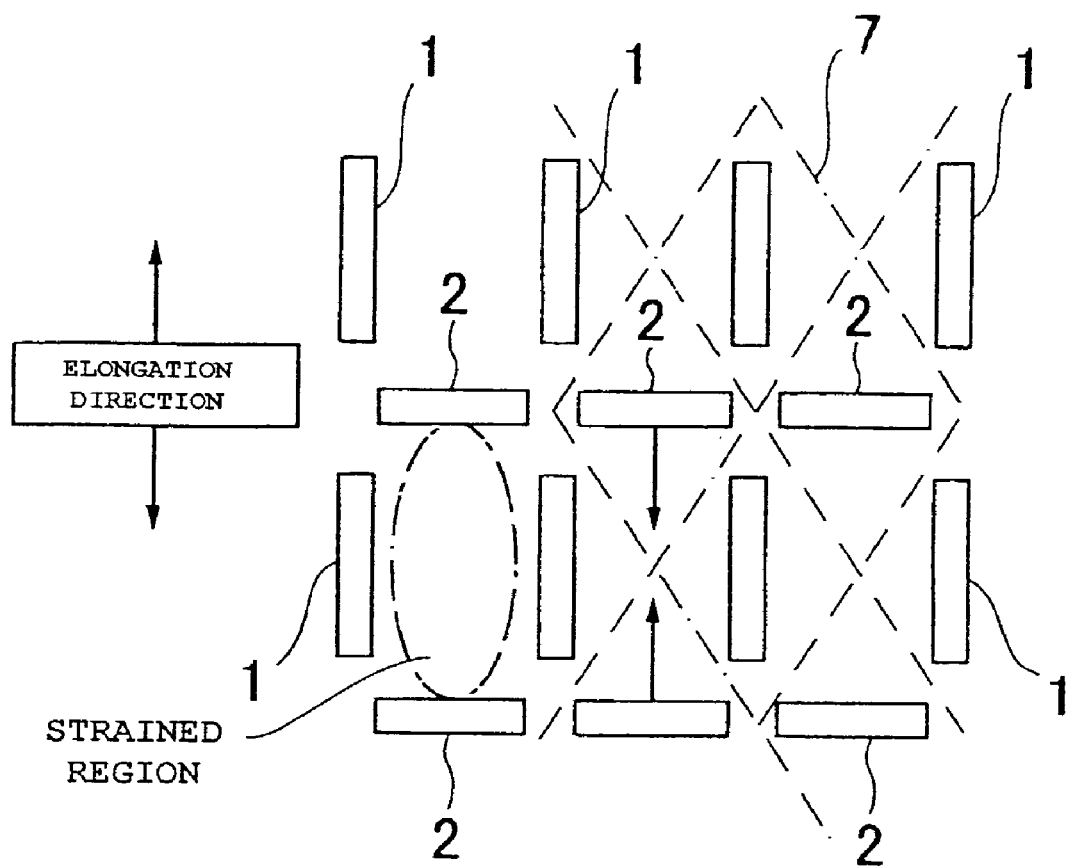
FIG. 2 is an illustration showing the principle of formation of the convex-concave wrinkles.
Figure 3:
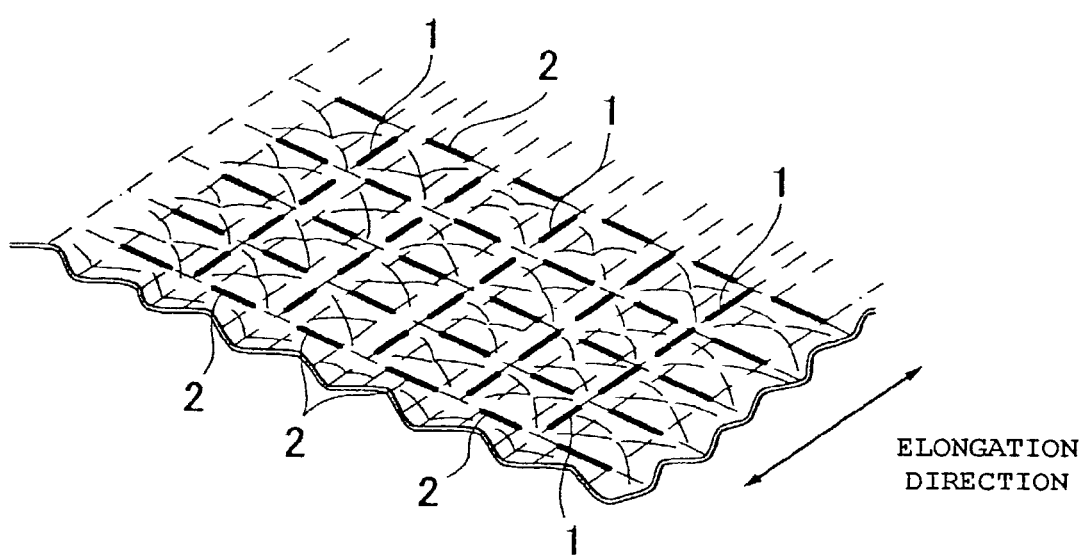
FIG. 3 is a perspective view of a main part of a plastic sheet in which melt patterns are formed.

The diffusion direction of the foregoing strains, in other words, the virtual lines (7)(hereinafter referred as to "strain-releasing lines") in the approximately elongation direction and bonding the regions where no melt pattern is formed are, as shown in FIG. 2, linearly discontinuous in the elongation direction but form diamond patterns.

The wrinkles formed owing to internal stresses corresponding to the arrangements of the foregoing melt patterns do not restore the original flat plane state even if being pressurized during the use but almost permanently keep the wrinkled state.

Incidentally, inventors of the invention have confirmed the wrinkle generation states in the case of forming only the holding patterns 1 and in the case of forming only the disconnecting patterns 2 in order to separately investigate the functions of the foregoing holding patterns 1 and the disconnecting patterns 2.

Figure 4A:
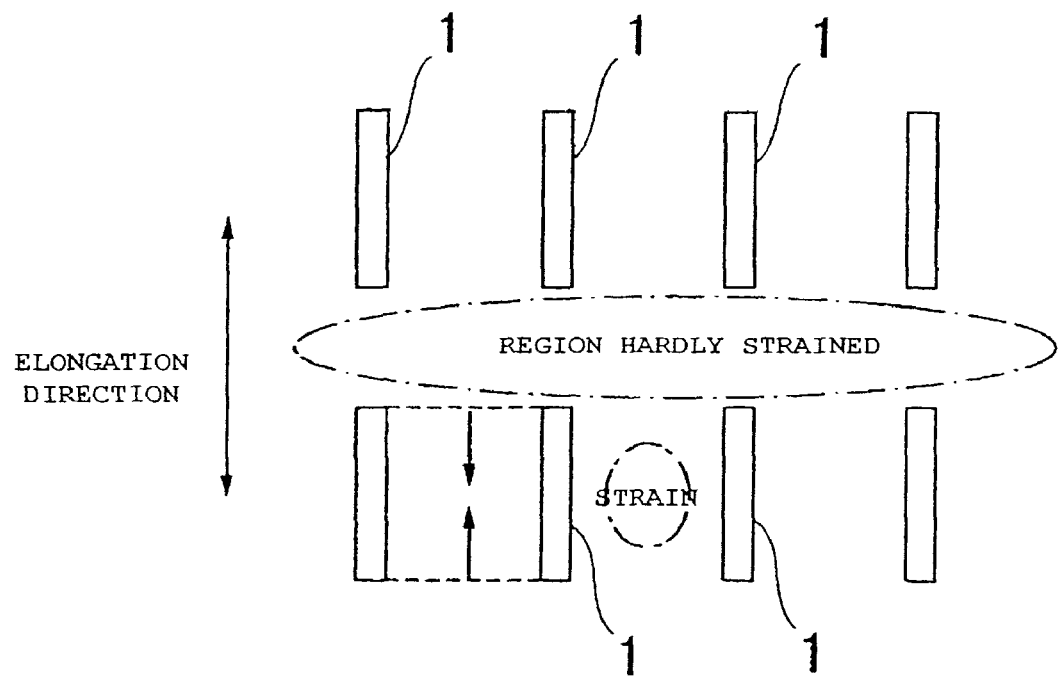
FIG. 4A is an illustration showing the wrinkle-formed state in the case of forming only holding patterns 1 and FIG. 4B is an illustration showing the wrinkle-formed state in the case of forming only disconnecting patterns 2.

FIG. 4A shows an example of the case of forming only the holding patterns 1 and it has been found that since the strains generated by the holding patterns 1 are diffused in the up and down direction (in the elongation direction), the strains are generated only in extremely narrow ranges in the peripheral parts of the holding patterns 1 and irregular projected parts and recessed parts are hard to be formed.

Figure 4B:
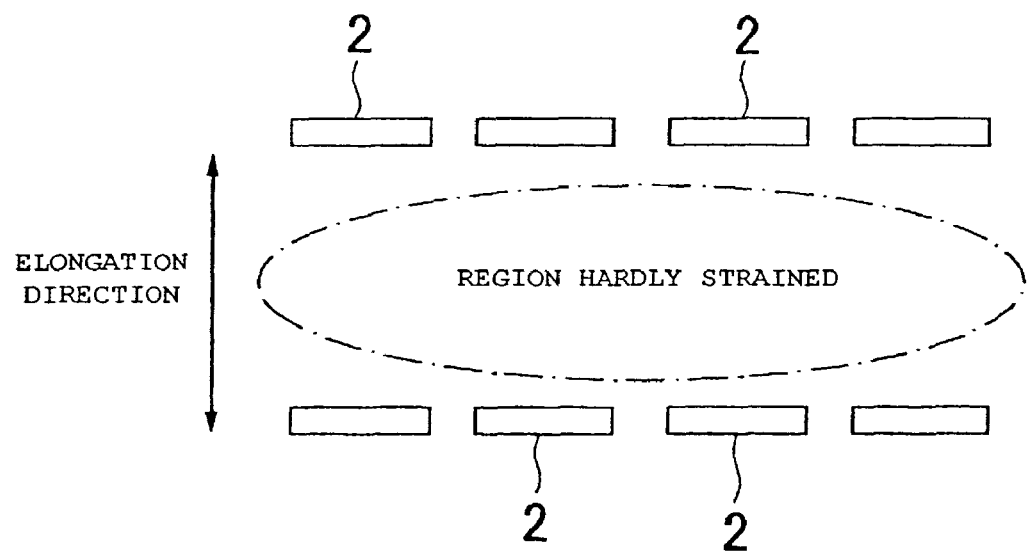

On the other hand, in the case of forming only disconnecting patterns 2 as shown in FIG. 4B, it has been found that since strains are hardly generated, wrinkles are scarcely formed.

The longitudinal size of the foregoing holding patterns 1 in the elongation direction is preferably in a range of 1.5 to 7 mm. If it is shorter than 1.5 mm, the strains are too small to outstandingly form the convex-concave wrinkles and if it is longer than 7 mm, although the strains owing to the holding patterns 1 are sufficiently high, it will be understood from that the shapes of the foregoing strain-releasing lines 7 become big, the projected parts and the recessed parts become smooth and preferable cloth-like appearance cannot be obtained.

[The Second Formation Mode]

Figure 5:
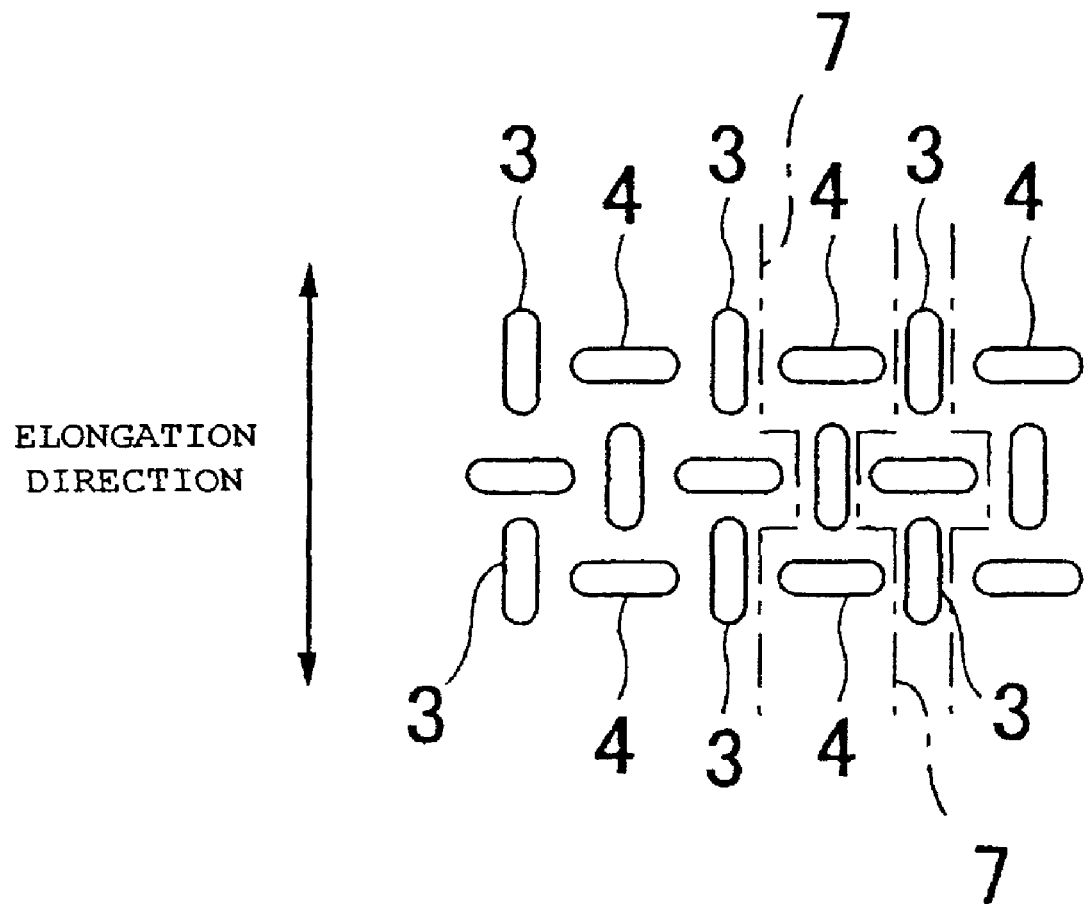
FIG. 5 is a plan view showing the second embodiment of melt patterns.

The melt patterns according to the second formation mode, as shown in FIG. 5 are formed by repeating melt pattern arrangements in lattice-like pattern state in the elongation direction, in which each melt pattern arrangement, different from the first formation mode of reciprocally forming the rows of holding patterns 1 and the rows of disconnecting patterns 2 in the elongation direction, is formed by reciprocating the holding patterns 3 at predetermined intervals in the direction perpendicular to the elongation direction and practically having the longitudinal size in the elongation direction to hold the elongation state and disconnecting patterns 4 practically having the longitudinal size in the direction perpendicular to the elongation direction to shut the diffusion of the strains owing to the holding patterns 3 in the elongation direction in a manner of forming the zigzagged pattern state in the elongation direction.

The functions of the foregoing holding patterns 3 and the disconnecting patterns 4 are as described above, even in such a formation mode, since the zigzagged strain-releasing lines 7 are formed, irregularly convex-concave wrinkles can be formed corresponding to the foregoing melt patterns.

[The Third Formation Mode]

Figure 6:
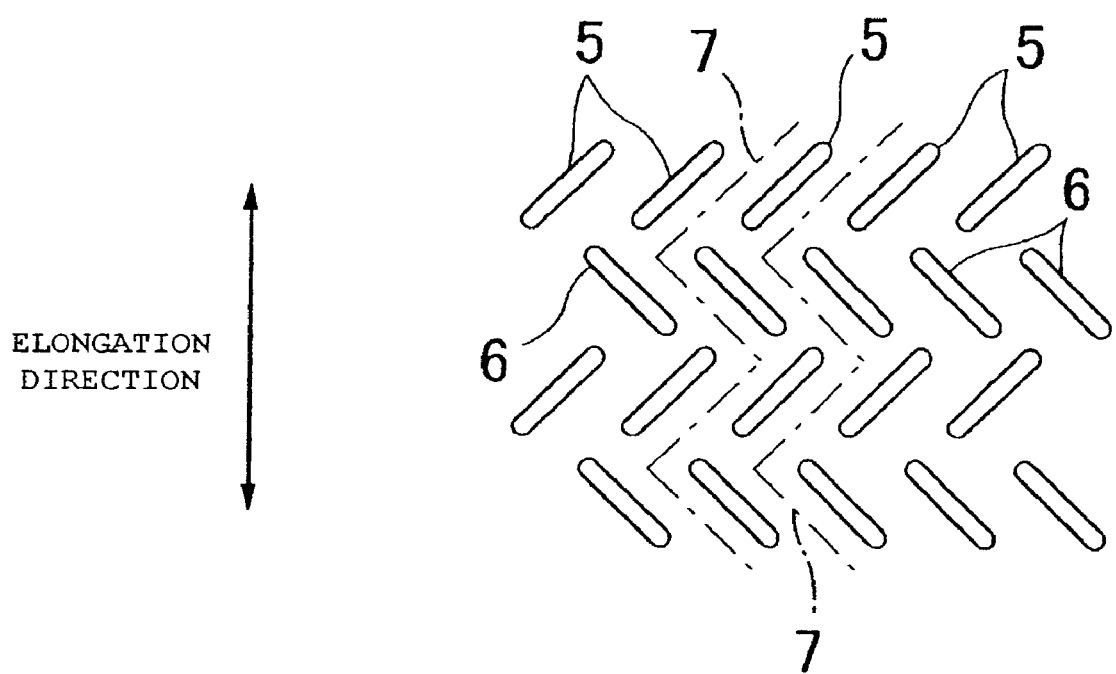
FIG. 6 is a plan view showing the third embodiment of melt patterns.

In the melt patterns according to the third formation mode, as shown in FIG. 6, being different from the first formation mode, the holding patterns 1 and the disconnecting patterns 2 cannot clearly be distinguished from each other, however the strain-releasing lines 7 are made zigzag so as to form the convex-concave wrinkles corresponding to the foregoing melt pattern arrangement in a plastic sheet face.

To described in details, the melt patterns are formed in the condition of elongating the foregoing plastic sheet by repeatedly reciprocating rows of first melt patterns 5 formed in columns-like state at predetermined intervals in the direction perpendicular to the elongation direction and practically having the longitudinal size in the direction slanting to the elongation direction and rows of second melt patterns 6 formed like columns positioned between respectively neighboring patterns of the rows of the first patterns at predetermined intervals in the direction perpendicular to the elongation direction and practically having the longitudinal size in the direction crossing the elongation direction and the slanting direction of the first melt patterns (5).

Such the first melt patterns 5 and second melt patterns 6 respectively have longitudinal components in the elongation direction and have the function as same as that of the holding patterns 1 in the first formation mode example and also have longitudinal components in the direction perpendicular to the elongation direction and have the function as same as that of the disconnecting patterns 2 in the first formation mode example.

Even with such melt pattern formation mode, as shown in FIG. 6, the direction of the releasing lines 7 for releasing stains generated in the first melt patterns 5 and the second melt patterns 6 do not become linear in the elongation direction but become zigzag and many strains internally remain as residual strains, so that irregular convex-concave wrinkles can be formed.

[The Fourth Formation Mode]

Figure 7A:
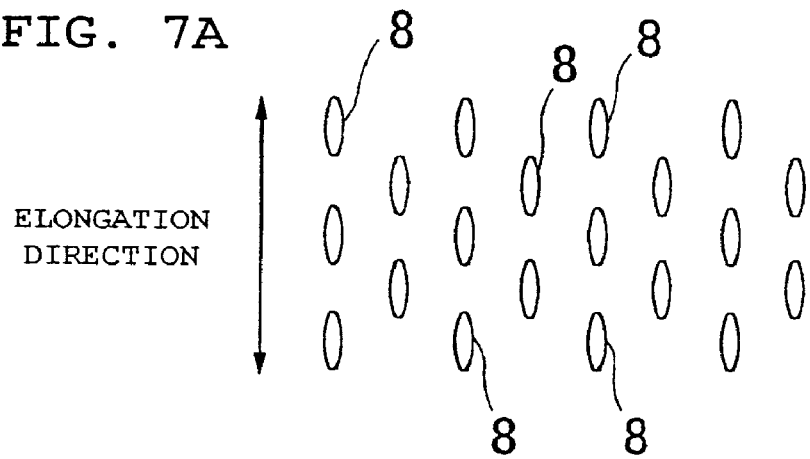
FIGS. 7A to 7C are plan views showing the fourth embodiment of melt patterns.
Figure 7B:
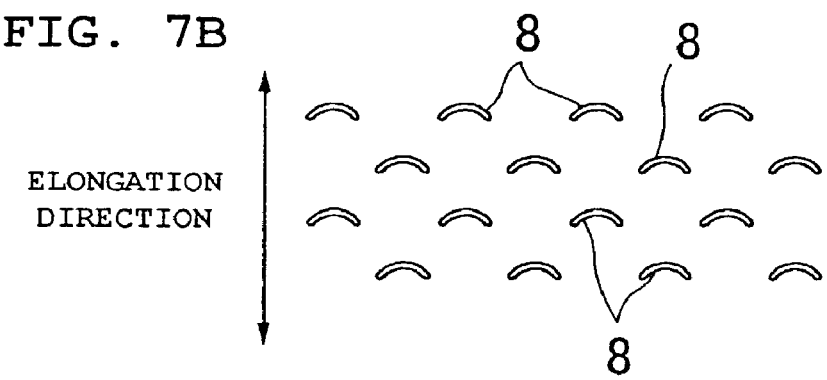
Figure 7C:
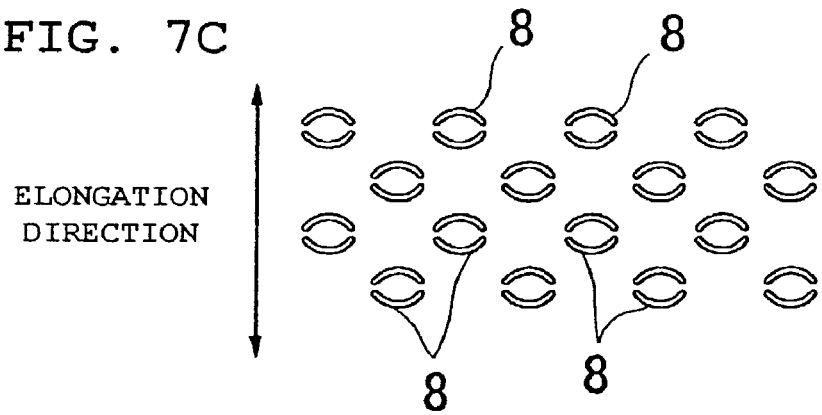

Next, melt patterns according to the fourth formation mode example shown in FIGS. 7A to 7C are formed by arranging patterns with predetermined shapes or designs in non-lattice-like arrangement on the sheet face under the condition of elongating the plastic sheet so as to form convex-concave wrinkles corresponding to the foregoing melt pattern arrangements in the plastic sheet face.

Figure 8:
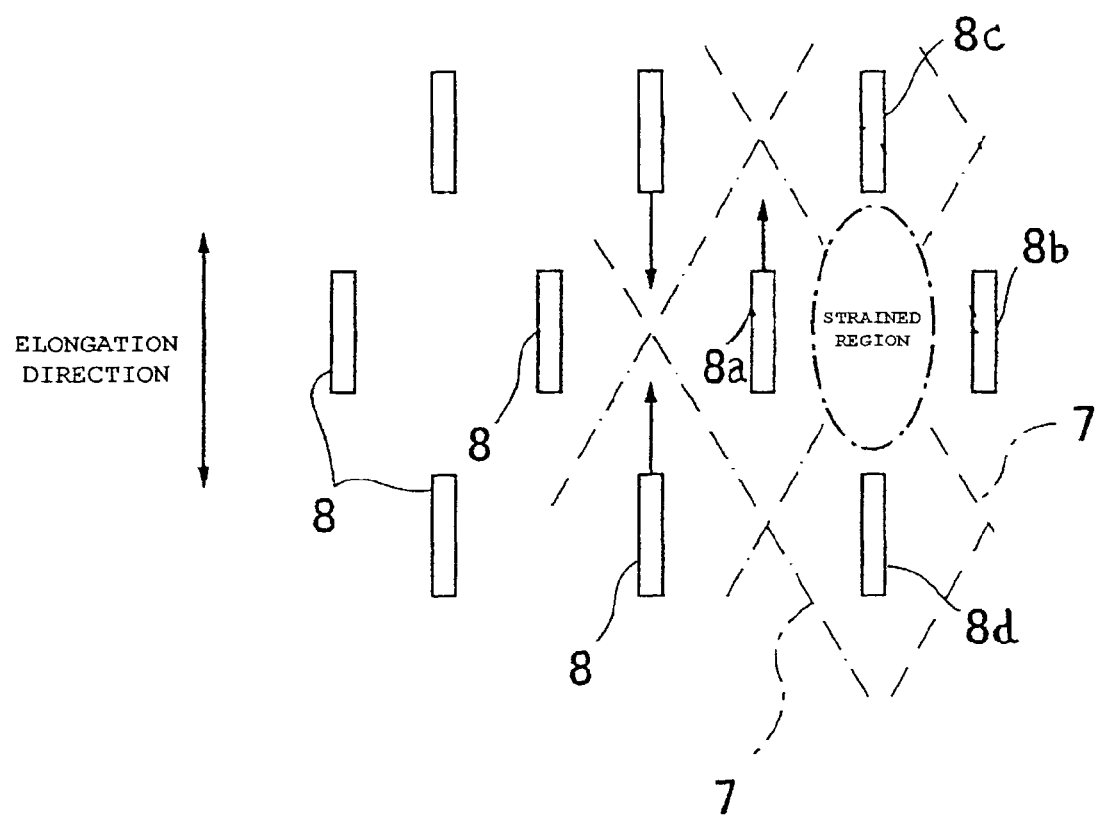
FIG. 8 is an illustration showing the principle of formation of the convex-concave wrinkles.

To describe practically based on FIG. 8, melt patterns 8 with the same shapes or designs are non-lattice state, in the illustrated example, in zigzagged state. The melt patterns 8a, 8b neighboring in the horizontal direction (in the direction perpendicular to the elongation direction) bear the function same as that of the holding patterns 1 in the first formation mode example and melt patterns 8c, 8d positioned in the upper and lower parts in the middle of the foregoing neighboring the melt patterns in the horizontal direction bear the function same as that of the disconnecting patterns 2 in the first formation mode example, so that strains generated in regions each surrounded with four melt patterns 8a, 8d, 8b, 8c positioned in up and down and right and left are diffused in the direction of the diamond-shape strain-releasing lines 7 shown in the same figure and at the same time many strains remain internally as residual strains, so that irregularly undulated convex-concave wrinkles can be formed.

[Manufacturing Method]

Formation of the melt patterns in order to obtain the foregoing plastic sheet according to the present invention is carried out in the conditions of elongating the plastic sheet, and at that time, while the tension being applied at 5 to 40% elongation, preferably 10 to 30% elongation, the melt patterns are formed by a melt pattern-forming roll heated to the softening point of the plastic sheet and then the tension is released.

If the elongation is less than 5%, strains sufficient to form convex-concave wrinkles cannot be formed and if the elongation is higher than 40%, although it depends on the material and the thickness of the sheet, the sheet is elongated too a far extent to restore the shape or in some cases the sheet is torn out depending on the melt patterns and thus it is not preferable.

<The Surface Material of the Absorptive Product>

Next, the following is the description of a plastic sheet having the foregoing cloth-like appearance to be used as a surface material of an absorptive product.

Figure 9:
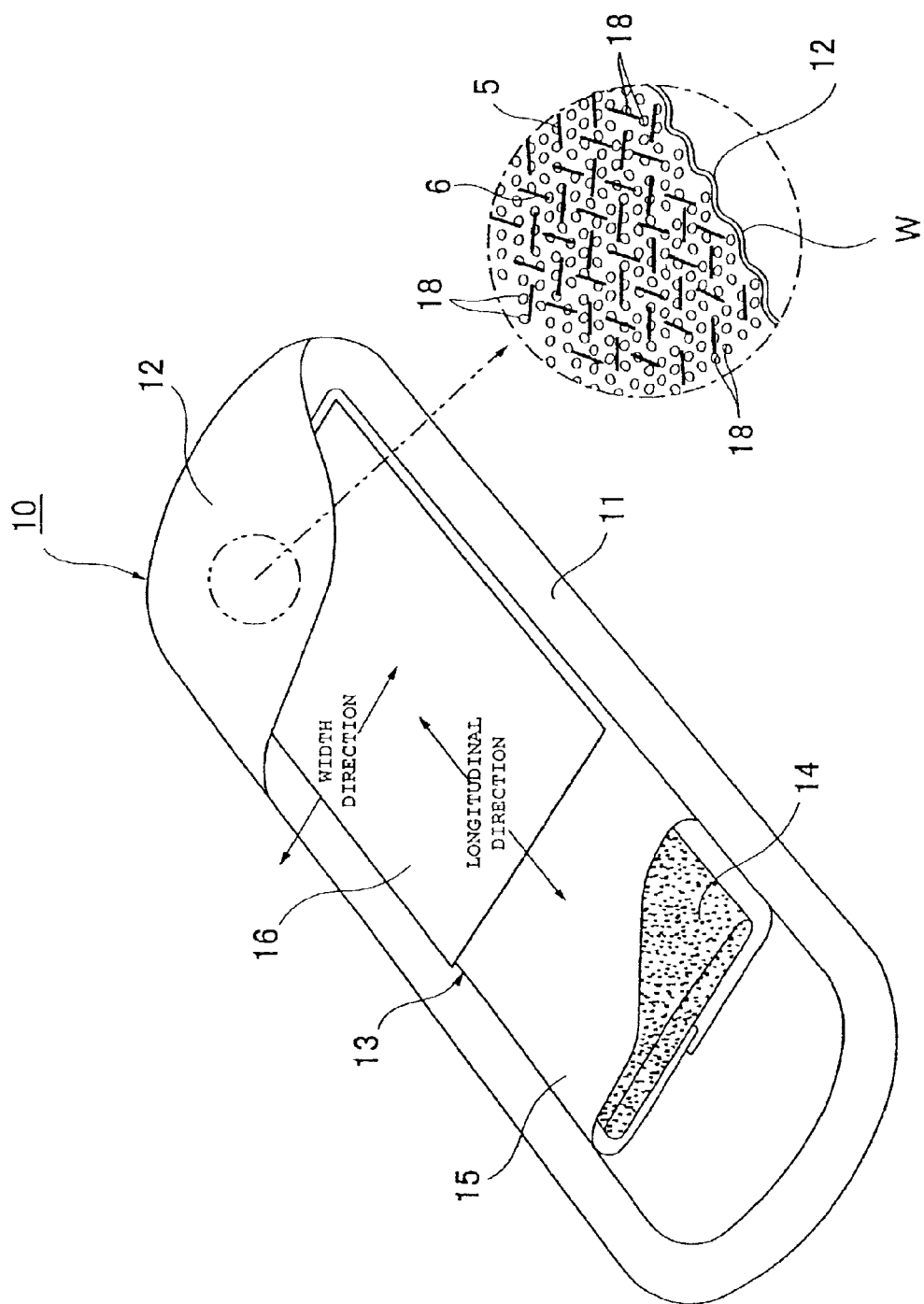
FIG. 9 is a partially ruptured perspective view showing an example of an absorptive product.

As shown in FIG. 9, an absorptive product 10 is to be applied for the uses of mainly a panty liner, a sanitary napkin, a sheet for a discharge from the womb, a pad for incontinence or the like and has a constitution composed by inserting either an absorptive body 14 or an absorptive unit 13 composed of the foregoing absorptive body 14 and crape paper 15 surrounding the absorptive body between a liquid-impermeable rear face sheet 11 and a liquid-permeable surface sheet 12(hereinafter simply referred also as to "a surface sheet") as shown in the same figure. In the illustrated example, since a sheet made of a thermoplastic resin having a large number of opening holes 18 is used as the foregoing surface sheet 12, a second sheet 16 made of a hydrophilic non-woven fabric is inserted between the absorptive unit and the sheet 12 in order to promote diffusion and absorption of the body fluid and prevent return of the body fluid. Incidentally, the second sheet 16 may previously be laminated and integrated with the surface sheet 12.

For the foregoing liquid-impermeable rear face sheet 11, usable is a sheet material of polyethylene, polypropylene or the like having at least water-proofness and from the viewpoint of preventing the stuffiness, those having water vapor permeability recently tend to be used preferably.

As the foregoing absorptive body 14, any materials are usable if they are capable of absorbing and retaining the body fluid and generally, those containing fluff-like pulps mixed with an absorptive polymer powder are preferable to be used in terms of the absorptive functions and the cost. The foregoing absorptive body 14 is preferable to be surrounded with the crape paper 15 in order to keep the shape and quickly diffuse the menstrual blood and the like and at the same time to prevent return of once absorbed menstrual blood and the like. Further, the plane shape of the absorptive body 14 may be an elliptical shape or a fit-cut shape (gourd-shaped), as illustrated, in order to moderate touch to the hip joint.

As the surface sheet 12 in this absorptive product 10, employed is a plastic sheet made of fusible and thermoplastic resin having the cloth-like appearance according to the present invention and a large number of opening holes 18 for liquid permeation are formed in order to provide liquid permeability. The diameter of the opening holes 18 for liquid permeation is 0.05 to 2.0 mm, preferably 0.1 to 1.0 mm, and the number of the opening holes is preferably adjusted to be 200 to 500/cm$^2$. The methods for forming the foregoing opening holes 18 may be a method comprising steps of softening the synthetic resin sheet at a temperature close to the softening temperature and while disposing the synthetic resin sheet on a supporting body having a large number of opening holes, sucking the resin sheet from the lower side of the supporting body or having a large number of opening holes, by a method comprising a step of pressurizing the resin sheet with air pressure from the upper face of the supporting body, by a method comprising a step of stamping a large number of slits in a synthetic resin sheet material and then opening the opening holes by elongating the sheet material and other proper methods are applicable.

Together with a large number of liquid-permeable opening holes 18 in predetermined portions, preferably in the entire surface, of the foregoing surface sheet 12, the melt patterns 5 and 6 are formed between neighboring opening holes as to enclose the regions among the opening holes and at the same time convex-concave wrinkles corresponding to the arrangements of the melt patterns 5 and 6.

Figure 10:
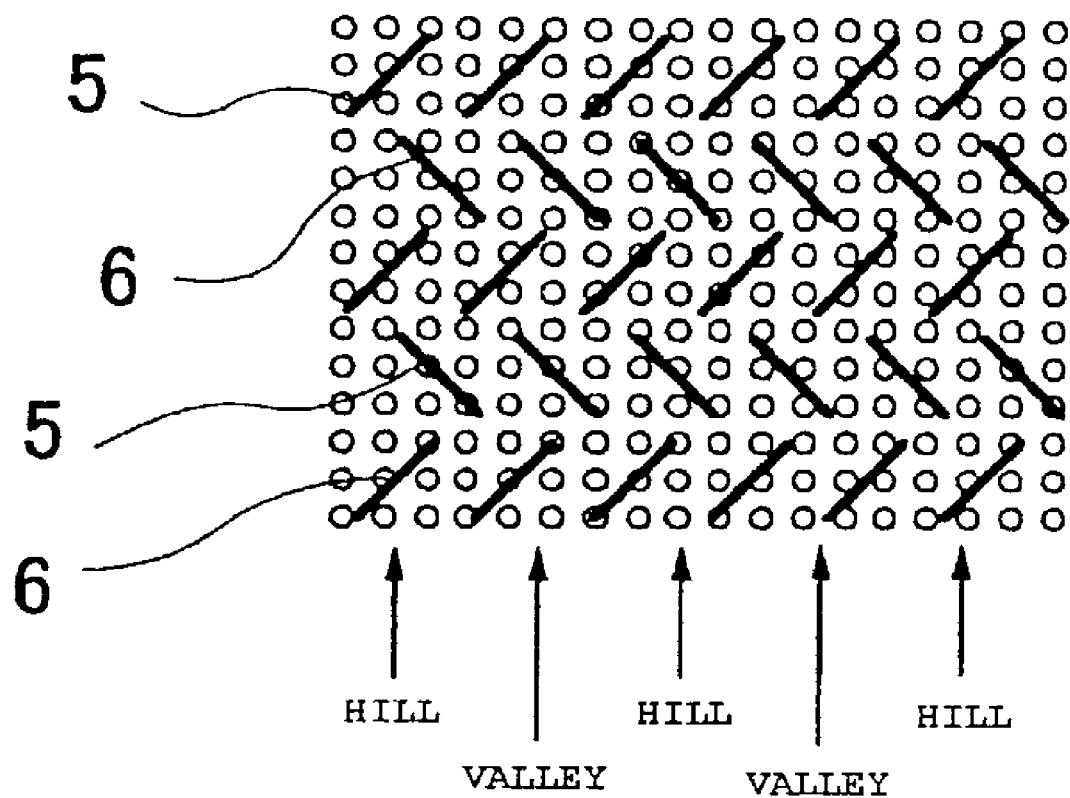
FIG. 10 is a main plan view of a surface sheet 12.
Figure 11:
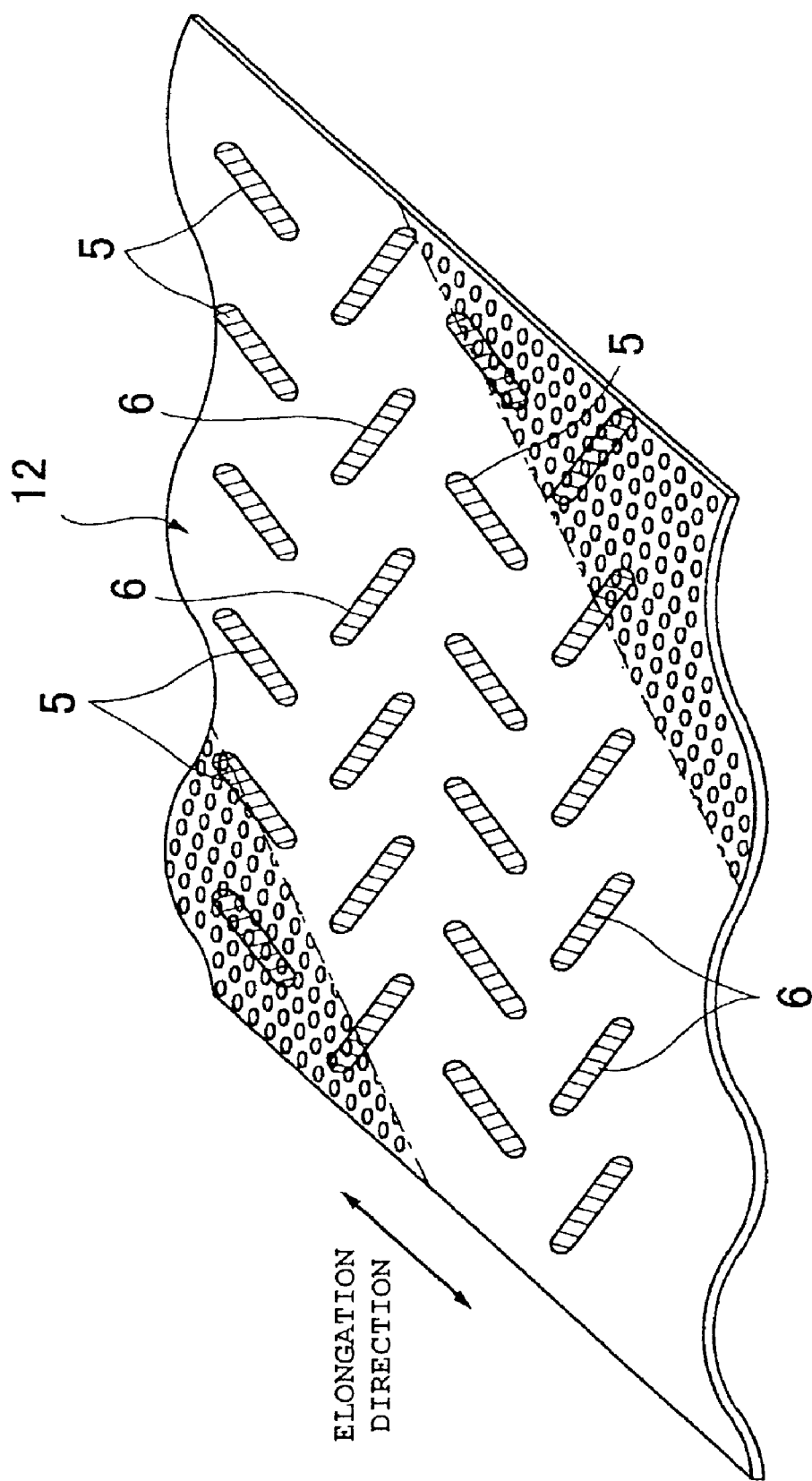
FIG. 11 is a perspective view of a surface sheet 12.

The foregoing melt patterns 5 and 6 are, so to say, examples of the melt patterns according to the foregoing third formation mode formed by repeatedly reciprocating rows of the first melt patterns 5 inclining up rightward and rows of the second melt patterns 6 inclining down rightward, as illustrated in FIG. 10, while elongating the plastic sheet. Owing to these melt patterns 5 and 6, the virtual lines virtual lines in the approximately elongation direction and bonding the regions where no melt pattern is formed are linearly discontinuous but continuously zigzagged and thus convex-concave wrinkles W are formed corresponding to the melt pattern arrangements.

Incidentally, the corresponding relationship of the foregoing melt patterns 5 and 6 and the wrinkles W are illustrated in FIG. 10, however that is only one general example and some cases, the hills and the valleys may be reversed.

The foregoing melt patterns 5 and 6 can be formed by pushing the foregoing emboss roll heated to a temperature near to the softening point of the surface sheet while applying tension to the surface sheet 12 in one direction at the time of the foregoing melt pattern formation and then releasing the tension. Incidentally, the tension may be applied not only in one direction but also in two directions.

The light reflectance in the skin-contacting face side of the foregoing surface sheet 12 is preferably 5% or lower to have the cloth-like appearance. If the light reflectance exceeds 5%, the luster feel of a plastic sheet becomes outstanding and it gives a cool impression and thus is not preferable. Incidentally, the light reflectance is defined as "the ratio of the intensity of reflected light to the intensity of the impingent light" and practically a numeral value obtained by measuring the intensity of the light reflected from the napkin surface material by a photometer and calculating the ratio of the measured intensity to the intensity of reflected light from the mirror in the case the reflecting capability of a standard mirror face is assumed to be "100".

Figure 12:
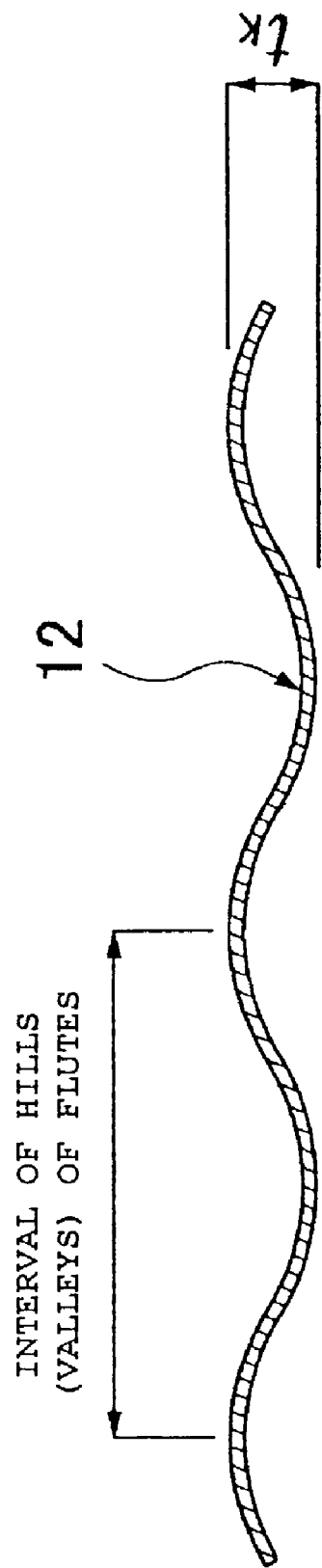
FIG. 12 is a cross-sectional view of a surface sheet 12.

On the other hand, the apparent thickness $t_k$ of the surface sheet 12 containing the hill parts and valley parts of the foregoing wrinkles W, as shown in FIG. 12, is preferable to 5 mm or thinner. If the apparent thickness $t_k$ exceeds 5 mm, although the cloth-like feel can be provided, the convex-concave degree becomes high so that an impression of the stiff surface is increased. Further, since the elongation degree of the surface sheet 12 has to be increased at the time of forming the melt patterns, it becomes difficult to control the tension during the manufacturing process.

Further, the intervals between neighboring hills or valleys of the foregoing wrinkles are preferably 10 mm or narrower. If the inter-hill (or valley) intervals exceed 10 mm, the flat parts per unit surface area increases and the plastic sheet feel is increased and the cloth-like feel is decreased.

Figure 13:
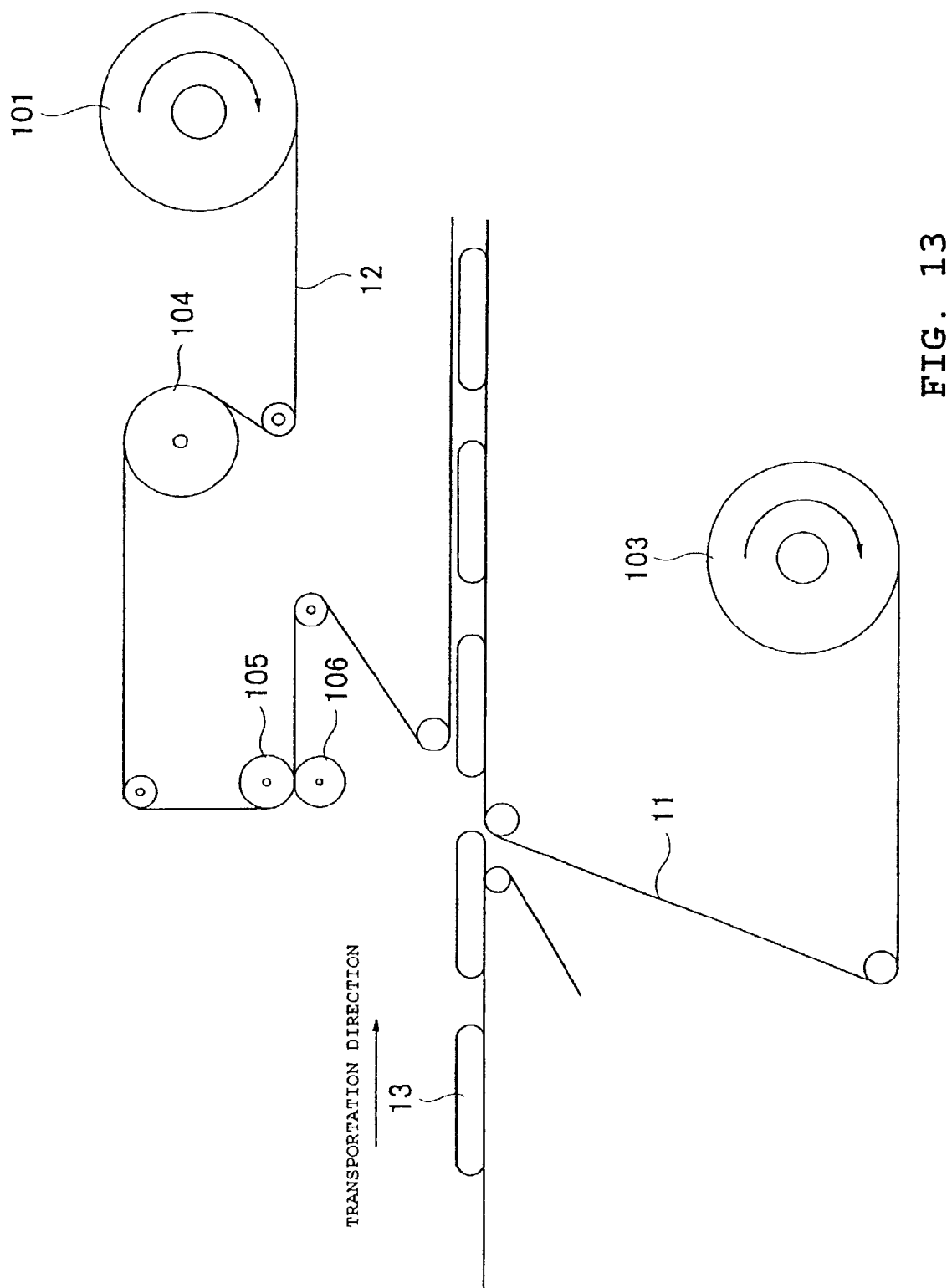
FIG. 13 is a schematic figure showing the manufacturing method of an absorptive product using the surface sheet.

On the other hand, in order to carry out assembly while an un-processed plastic being processed to be the foregoing surface sheet 12 in a manufacturing line of an absorptive product, for example, as illustrated in FIG. 13, the surface sheet 12 fed out of a surface material supply drum 101 is introduced into a hole-opening roll 104 having a large number of arranged holes and then heated to a temperature close to the softening point and simultaneously sucked through the hole-opening roll 104 to form a large number of opening holes 18.

Next, the surface sheet 12 in which the opening holes 18 are formed is led to an anvil roll 106 and while the tension being applied properly responding to the type of the material in the processing flow direction (and/or in rectangular direction) of the apparatus, the surface sheet is provided with melt patterns by an emboss roll 105 heated to a temperature close to the softening point of the surface material. After the melt pattern formation, the tension is released to form convex-concave wrinkles. After that, a rear face sheet 11 fed out of a rear face sheet supply drum 103 and an absorptive unit 12 are laminated on the resulting sheet to complete an absorptive product.

Incidentally, the manufacturing of the surface sheet 12 of the present invention is not restricted to the above described method but, for example, the opening holes in the foregoing surface sheet 12 may be carried out previously in the step by a maker of producing the surface sheet 12 and also, melt pattern formation and wrinkle manufacturing may be carried out simultaneously with the formation of the foregoing opening holes 18 in the step by a maker. In such a case, an absorptive product using the foregoing surface sheet can be produced without requiring any alteration of the already existing absorptive product manufacturing line where a surface sheet is used as it is.

Inventors of the present invention have formed a variety of types of melt patterns in polyethylene sheets and evaluated them by visual evaluation and skin touch evaluation. The evaluation is carried out by 5-grade evaluation; ⊚: excellently good, ◯: good, Δ: fairly good and X: inferior.

Figure 14:
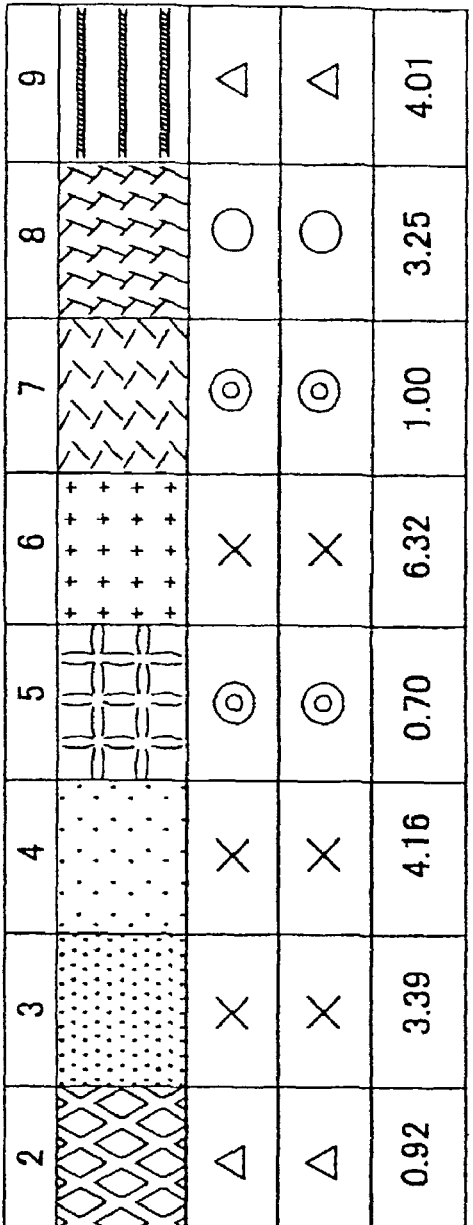
FIG. 14 is a table showing the results of comparative evaluations after forming a variety of melt patterns on polyethylene sheets.

Further, also measured is the reflecting capability indicating the degree of the diffused reflection of light in the surface of a synthetic resin sheet material. Since the reflecting capability is defined as "the ratio of the intensity of the reflected light to the intensity of the impingent light", the intensity of the light reflected by a mirror face and the intensity of the light reflected by a napkin surface material are measured by a photometer and their ratio is calculated. The numeral value is shown as % value of the reflecting capability of each sample in the case the reflecting capability of a standardized mirror is set to be "100". These results are shown in FIG. 14.

As the results of the test, samples of No. 5, 7 and 8 show relatively good results. On the other hand, melt patterns with dotted patterns show relatively inferior results. One characteristic of the melt pattern group with good results is that they have relatively large size to be seen visually and that rows of melt patterns having clear difference in pattern shapes in a predetermined direction such as the longitudinal direction or the width direction of the surface material are reciprocally arranged. In other words, those having reciprocally repeated two types of rows of patterns composed basically of liner or shaped patterns in cooperation with wrinkle formation show good results in both of the visual evaluation and the skin touch evaluation.

The invention claimed is:

1. A method for producing a plastic sheet having a cloth-like appearance, comprising:
    pulling and expanding a whole of a thermoplastic plastic sheet in one direction;
    applying melt patterns to the sheet while keeping the whole of the thermoplastic plastic sheet in an expanded state; and
    releasing the whole of the thermoplastic plastic sheet from the expanded state to generate strains in the whole of the thermoplastic plastic sheet and thereby form wrinkles on the whole of the thermoplastic plastic sheet.

2. The method of claim 1, wherein the melt patterns comprise:
    rows of holding patterns arranged in rows at selected intervals in a direction perpendicular to the expansion direction and have their longitudinal dimensions substantially in the expansion direction to maintain the expanded state; and
    rows of disconnecting patterns arranged in rows at selected intervals in a direction perpendicular to the expansion direction and have their longitudinal dimensions substantially in a direction perpendicular to the expansion direction to disconnect a diffusion of strains generated by the holding patterns in the expansion direction; wherein
    the rows of the holding patterns and the rows of the disconnecting patterns are arranged alternately and repeatedly in the expansion direction.

3. The method of claim 1, wherein the melt patterns comprise:
    holding patterns having their longitudinal dimensions substantially in the expansion direction to keep the expanded state; and
    disconnecting patterns having their longitudinal dimensions substantially in a direction perpendicular to the expansion direction to disconnect a diffusion of strains generated by the holding patterns in the expansion direction, and that are arranged alternately in rows at selected intervals in the direction perpendicular to the expansion direction; wherein
    the formed melt patterns are arranged in the expansion direction to form a repeating zigzag pattern.

4. The method of claim 1, wherein the melt patterns comprise:
    rows of first melt patterns formed in rows at selected intervals in the direction perpendicular to the expansion direction, and having their longitudinal dimensions substantially in a direction aligned with the expansion direction; and
    rows of second melt patterns formed in rows at selected intervals in a direction perpendicular to the expansion direction, and having longitudinal dimensions substantially in a direction aligned with the opposite direction of the expansion direction; wherein
    the rows of the first melt patterns and the rows of the second melt patterns are arranged alternately and repeatedly in the expansion direction.

5. The method of claim 1, wherein the melt patterns are formed of patterns having a selected shape or design and arranged in a non-lattice pattern.

6. A method for producing a plastic sheet having a cloth-like appearance, comprising:
    expanding a whole of a thermoplastic plastic sheet in a selected expansion direction by 5% to 40%;
    applying melt patterns to the whole of the expanded sheet with a melt pattern applying roll heated up to the softening point of the thermoplastic plastic sheet; and
    releasing the whole of the thermoplastic plastic sheet from the expanded state to generate strains in the whole of the thermoplastic plastic sheet and thereby form wrinkles on the whole of the thermoplastic sheet.

7. The method of claim 6, wherein the melt patterns comprise:
   rows of holding patterns arranged in rows at selected intervals in a direction perpendicular to the expansion direction and having longitudinal dimensions substantially in the expansion direction to keep the expanded state; and
   rows of disconnecting patterns arranged in rows at selected intervals in a direction perpendicular to the expansion direction and having longitudinal dimensions substantially in a direction perpendicular to the expansion direction to disconnect a diffusion of strains generated by the holding patterns in the expansion direction; wherein
   the rows of the holding patterns and the rows of the disconnecting patterns are arranged alternately and repeatedly in the expansion direction.

8. The method of claim 6, wherein the melt patterns comprise:
   holding patterns having their longitudinal dimensions substantially in the expansion direction to keep the expanded state; and
   disconnecting patterns having their longitudinal dimensions substantially in a direction perpendicular to the expansion direction to disconnect a diffusion of strains generated by the holding patterns in the expansion direction, and that are arranged alternately in rows at selected intervals in the direction perpendicular to the expansion direction; wherein
   the formed melt patterns are arranged in the expansion direction to form a repeating zigzag pattern.

9. The method of claim 6, wherein the melt patterns comprise:
   rows of first melt patterns formed in rows at selected intervals in the direction perpendicular to the expansion direction, and having their longitudinal dimensions substantially in a direction aligned with the expansion direction; and
   rows of second melt patterns formed in rows at selected intervals in a direction perpendicular to the expansion direction, and having longitudinal dimensions substantially in a direction aligned with the opposite direction of the expansion direction; wherein
   the rows of the first melt patterns and the rows of the second melt patterns are arranged alternately and repeatedly in the expansion direction.

10. The method of claim 6, wherein the melt patterns are formed of patterns having a selected shape or design and arranged in a non-lattice pattern.

* * * * *